(12) United States Patent
Kiniwa

(10) Patent No.: US 8,247,458 B2
(45) Date of Patent: Aug. 21, 2012

(54) THERAPEUTIC AGENT FOR DIABETIC NEUROPATHY

(75) Inventor: Mamoru Kiniwa, Tokushima (JP)

(73) Assignee: Taiho Pharmaceutical Co., Ltd., Tokyo (JP)

( * ) Notice: Subject to any disclaimer, the term of this patent is extended or adjusted under 35 U.S.C. 154(b) by 152 days.

(21) Appl. No.: 12/448,590

(22) PCT Filed: Dec. 20, 2007

(86) PCT No.: PCT/JP2007/075233
§ 371 (c)(1),
(2), (4) Date: Jun. 26, 2009

(87) PCT Pub. No.: WO2008/078826
PCT Pub. Date: Jul. 3, 2008

(65) Prior Publication Data
US 2010/0041764 A1   Feb. 18, 2010

(30) Foreign Application Priority Data

Dec. 26, 2006   (JP) ................................ 2006-349987

(51) Int. Cl.
*A01N 31/00* (2006.01)
*A61K 31/10* (2006.01)
*C07C 319/00* (2006.01)
*C07C 321/00* (2006.01)
*C07C 323/00* (2006.01)
*C07C 381/00* (2006.01)

(52) U.S. Cl. ......................................... 514/712; 568/38

(58) Field of Classification Search .................. 514/712; 568/38
See application file for complete search history.

(56) References Cited

U.S. PATENT DOCUMENTS

| | | | |
|---|---|---|---|
| 4,556,737 A * | 12/1985 | Koda et al. | .................... 564/218 |
| 6,329,428 B1 | 12/2001 | Yamauchi et al. | |
| 2004/0087558 A1 | 5/2004 | Zeldis et al. | |
| 2007/0161696 A1 | 7/2007 | Zeldis et al. | |

FOREIGN PATENT DOCUMENTS

WO    WO2004058709 A1 * 12/2002

OTHER PUBLICATIONS

Oda et. al., Life Sciences, 1999, Elsevier, vol. 65, No. 8, pp. 763-770.*
Simmons et. al., Current Opin. Neurol., 2002, Lippincott Williams & Wilkins, vol. 15, pp. 595-603.*
International Search Report dated Feb. 5, 2008 in the International (PCT) Application PCT/JP2007/075233 of which the present application is the U.S. National Stage.
English Abstract of JP 2006131521 published May 25, 2006.
English Abstract of JP 2006076958 published Mar. 23, 2006.
English Abstract of JP 2004292407 published Oct. 21, 2004.
English Abstract of JP 11315019 published Nov. 16, 1999.
English Abstract of JP 2005097220 published Apr. 14, 2005.
English Abstract of JP 2006199642 published Aug. 3, 2006.

* cited by examiner

*Primary Examiner* — Sreeni Padmanabhan
*Assistant Examiner* — Sarah Pihonak
(74) *Attorney, Agent, or Firm* — Wenderoth, Lind & Ponack, L.L.P.

(57) ABSTRACT

A therapeutic agent for the treatment of diabetic neuropathy which comprises (±)-[2-[4-(3-ethoxy-2-hydroxypropoxy) phenylcarbamoyl]-ethyl]dimethylsulfonium p-toluene-sulfonate of the formula (1) as an active ingredient.

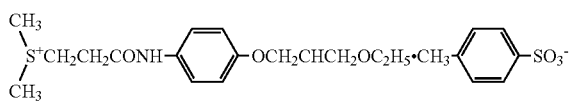

(1)

1 Claim, 1 Drawing Sheet

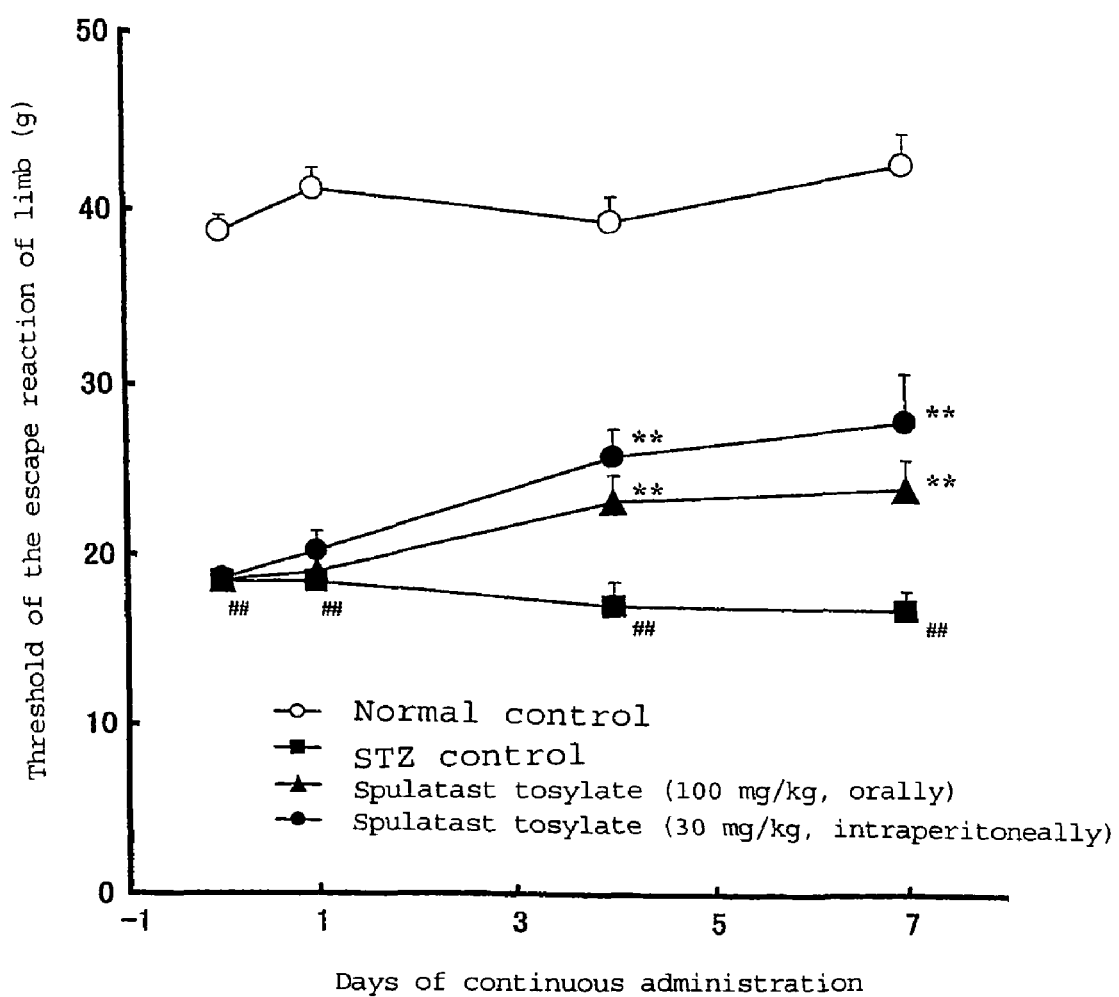

THERAPEUTIC AGENT FOR DIABETIC NEUROPATHY

TECHNICAL FIELD

The present invention relates to a therapeutic agent for diabetic neuropathy.

BACKGROUND ART

Diabetes is a dysbolism characterized by the chronic hyperglycemia which is caused by shortage of insulin and so on, and it is classified into Type 1 diabetes and Type 2 diabetes according to the cause of appearance of the symptoms. Type 1 diabetes is caused and initiated by the destruction of the insulin secretion cell of the pancreas by virus or the autoimmunity, and is often found in the youth. An environmental factor including lifestyle, such as overeating, obesity and lack of exercise as well as the aging become a cause of Type 2 diabetes, and the symptoms of Type 2 diabetes appear after the middle age. The number of patients suffering from diabetes is estimated about 7,400 thousand in Japan, and 90 to 95% of them are classified into Type 2 diabetes. If these diabetics are left without sufficient treatment and a hyperglycemia state continues for a long time, their QOL will not only be spoiled remarkably, but the symptoms of the critical complications in connection with a prognosis of life will also appear. Typical complications are diabetic retinopathy, diabetic nephropathy, and diabetes neuropathic disorder with which the present invention is concerned.

Diabetes neuropathic disorder is also called diabetic neuropathy, and about two thirds of diabetics are said to suffer from some kinds of complications. Generally an obstacle appears from the part (nerve of a hand or a tip of a foot) governed by long nerve fibers, and then is followed by numbness and a pain at hand and foot, and an unusual feeling cold in the beginning, and if they are left without any treatment, the condition progresses and spreads toward the bodily center such as from the tip of a foot to the knee and from the hand to the elbow. The diversity of such a symptom is caused by the factors that various kinds of nerves such as a motor nerve, a sensory nerve and an autonomous nerve are impaired, and that various functions are managed by each of the different nerves respectively, and these are the factors that make the diagnosis and treatment of the diabetic neuropathy difficult.

The mechanism of the development of diabetic neuropathy has not yet been established, but a promotion of the activity in polyol pathway as well as a dysbolism of myo-inositol that relates thereto, an abnormality of the activity of protein kinase C (PKC) and an oxidative stress are assumed to be metabolic factors. Another theory is also proposed that the insufficiency of the supplement of oxygen and nutrition to the nerve tissue by a microcirculation disturbance in the endoneurium is a vascular factor. It is supposed that these are not abnormal respectively, but a mutual interaction between the metabolic factors and the vascular factors causes the development and progress of the symptoms of diabetic neuropathy under the condition that a hyperglycemia state continues over a long period of time.

Regarding the prophylaxis and treatment of the diabetic neuropathy, a management of the risk factor, namely that of the diabetes condition, is the basic point, as is common to that of diabetic complications. On the other hand, the development of therapeutic agents in line with the development mechanism is also being carried on aggressively, and the usefulness of an inhibitor of the aldose reductase as a rate-controlling enzyme that promote the activation of the polyol metabolism, which is one of the metabolic factors, is expected. Moreover, it has been found that the activity of PKC (β-isoform) increases under the diabetic state or the hyperglycemia condition, and it is said that a selective PKC-β inhibitor suppresses hypoperfusion in the vasa nervorum which is one of the factors of the diabetic neuropathy. Furthermore, it has been reported that the cell damage by increase of oxidative stress and the hypoperfusion by inhibition of NO production cause the fall of nerve functions in recent years, and the effectiveness of the agents having various kind of anti-oxidative activities and the transcription factors located in the down stream of oxidative stress is reported from the basic point of view.

However, these agents on the basis of the cause of development of the disease are poor in efficacy against a developed neuropathy, and the necessity of an agent for the symptomatic treatment to improve the QOL of a patient is actually high. Especially, non-steroidal anti-inflammatory agent cannot be applied to the so-called diabetic neuropathy, such as pain, numbness and nociceptive hypersensitivity. Tricyclic antidepressants, anti-convulsants and mexiletine are said to be effective at present, but a decisive treatment has not been established yet. Therefore, the situation to make it possible to select an appropriate agent for symptomatic treatment according to the condition of the patient is expected.

An object of the present invention is to provide an agent which is almost free from harmful side effect and is very efficacious for the treatment of diabetic neuropathy, especially an agent for the treatment of a subjective symptom such as pain accompanied with a diabetic neuropathy.

DISCLOSURE OF THE INVENTION

The present invention relates to the following inventions:

1. A therapeutic agent for the treatment of diabetic neuropathy which comprises (±)-[2-[4-(3-ethoxy-2-hydroxypropoxy)phenylcarbamoyl]-ethyl]dimethylsulfonium p-toluenesulfonate of the formula (1) as an active ingredient.

(Compound 1)

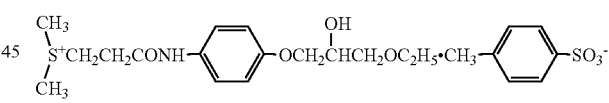

(1)

2. A therapeutic agent described in 1 mentioned above, wherein the diabetic neuropathy is a polyneuropathy.

3. A therapeutic agent described in 1 or 2 mentioned above, wherein a symptom of the diabetic neuropathy is throbbing pain and/or paresthesia.

4. Use of the compound of the formula (1) for producing a therapeutic agent for diabetic neuropathy.

5. A therapeutic method of diabetic neuropathy comprising administering to a mammal an effective amount of the compound of the formula (1).

(±)-[2-[4-(3-Ethoxy-2-hydroxypropoxy)phenylcarbamoyl]-ethyl]dimethylsulfonium p-toluenesulfonate (hereinafter abbreviated to "suplatast tosylate") shown by the formula (1) has an excellent suppressant action against IgE antibody production, and is known as an agent to treat bronchial asthma, atopic dermatitis and allergic rhinitis (JP1991-70698B: patent literature 1). Suplatast tosylate is also known as useful for an agent to treat urination trouble (WO00/27383: patent literature 2), an itchy curative agent accompanied with kidney dialysis (JP1999-315019A: patent literature 3), an improving agent for liver function unusually caused by C type or non B non C hepatitis virus (JP2002-114672A: patent literature 4), an agent to treat chemical sensitivity (JP2004-292407A: patent literature 5), a therapeutic agent for retroperitoneal fibrosis (JP2005-097220A: Patent literature 6), an agent for prophylaxis and/or treatment of lichen planus (JP2006-199642A: Patent literature 7), an agent for prophylaxis and/or treatment of headache (JP2006-131521A: Patent literature 8) and an agent for treatment of nephrotic syndrome (JP2006-076958A: Patent literature 9). However, it has not known at all that suplatast tosylate shows excellent effect as an agent for the treatment of diabetic neuropathy.

[Patent literature 1] JP1991-70698B
[Patent literature 2] WO00/27383
[Patent literature 3] JP1999-315019A
[Patent literature 4] JP2002-114672A
[Patent literature 5] JP2004-292407A
[Patent literature 6] JP2005-097220A
[Patent literature 7] JP2006-199642A
[Patent literature 8] JP2006-131521A
[Patent literature 9] JP2006-076958A Suplatast tosylate, which is the active ingredient of this invention, is a known compound, and is produced by the method described, for example, in JP1991-70698B.

The "medical treatment" as used in the present invention means the maintenance treatment for prevention and treatment of a disease as well as mitigation of condition accompanied by the disease and recurrence prevention.

The kinds of "diabetic neuropathy" that can be treated by the therapeutic agent of this invention are not limited specifically, but are any of neuropathy accompanied with a diabetes, and may be either a polyneuropathy (sensory neuropathy and motor neuropathy) or an autonomous neuropathy. Moreover, as for "the symptoms" to be treated by the therapeutic agent of this invention, throbbing pain, sensory paralysis, anesthesia (sensory loss), sensory abnormality (numbness, burning, feeling cold) and calf cramp are exemplified as the symptoms of the polyneuropathy, and gastrointestinal disorders (constipation/diarrhea), abnormal sweating, orthostatic hypotension, bladder disorder, erectile dysfunction are exemplified as the symptoms of the autonomous neuropathy.

As for the agent administered together with suplatast tosylate in this invention, aldose reductase inhibitors, antiarrhythmic agents, vitamins, non-steroidal anti-inflammatory agents, antidepressants, antipsychotic agents and anticonvulsants may be mentioned. Since the medical treatment effect of a pain accompanied with the diabetic neuropathy not only improves further by using together or more with these agents, but the amount of medication can be reduced compared with the case where it is used by the medicine independent which can be used together, it is suitable also from the view point of mitigation of side effects. Moreover, nerve block, acupuncture therapy, thermo-therapy, iontophoresis, nerve root block, ultra short-waves treatment, infrared irradiation treatment and laser irradiation treatment etc. may be used together with.

Examples of aldose reductase inhibitors are epalrestat and a pharmaceutically acceptable salt thereof.

Examples of antiarrhythmic agents are mexiletine and a pharmaceutically acceptable salt thereof.

Examples of vitamins are vitamin A, vitamin D, vitamin B analogs, (B1, B2, B6, B12), Niacin, folic acid, pantothenic acid, vitamin C, vitamin E, biotin and vitamin K, and more specifically preferable examples are retinol, a calcidol, calcitriol, tacalcitriol, calcipotriol, maxacalcitol, falecalcitol, thiamine, cocarboxylase, fursultiamine, prosultiamine, octotiamine, thiaminedisulfide, bisbentiamine, bisibutiamine, benfotiamine, cetotiamine, riboflavin, flavin adenine dinucleotide, pyridoxine, pyridoxal, nicotinic acid, nicotinamide, cyanocobalamin, cobamamide, mecobalamin, folic acid, calcium pantothenate, panthenol, panthetine, ascorbic acid, tocophenol, biotin, phytonadione, menatetrenone or a pharmaceutically acceptable salt thereof.

Examples of non-steroidal anti-inflammatory agents are sodium salicylate, acetylsalicylic acid, salicylamide, flufenamic acid, mefenamic acid, tolfenamic acid, diclofenac, sulindac, fenbufen, amfenac, indometacin, proglumetacin, acemetacin, nabumetone, etodolac, mofezolac, ibuprofen, ketoprofen, flurbiprofen, oxaprozin, fenobufen, tiaprofenic acid, naproxen, pranoprofen, loxoprofen, alminoprofen, zaltoprofen, bucolome, piroxicam, ampiroxicam, tenoxicam, lornoxicam, epirizole, tiaramide, emorphan and a pharmaceutically acceptable salt thereof.

Examples of anti-depressants are nortriptyline, amoxapine, maprotiline, imipramine, amitriptyline, trimipramin, clomipramine, lofepramin, dosulepin, trazodon, fluvoxamine, paroxetine, milnacipran, mianserin, setiptiline, sulpiride and a pharmaceutically acceptable salt thereof.

Examples of antipsychotic agents are fluphenazine, chlorpromazine and their pharmaceutically acceptable salts.

Examples of anti-spasm agents are phenyloin, ethotoin, phenobarbital, primidone, valproic acid, carbamazepin, trimethadione, ethosuximide, acetylpheneturide, sultiame, diazepam, clonazepam, clobazam, zonisamide, acetazolamide and a pharmaceutically acceptable salt thereof.

Examples of pharmaceutically acceptable salts in this invention are inorganic acid salt such as hydrochloride, sulfate, tartrate, hydrobromide, nitrate or phosphate; organic acid salt such as propionate, dipropionate, valerate, butyrate, pivalate, acetate, benzoate, mesylate, trifluoroacetate, tartrate, succinate, palmitate, citrate, malate, maleate, fumarate, methanesulfonate, benzenesulfonate, toluenesulfonate or nicotinate; and inorganic salt such as potassium salt, sodium salt, calcium salt or aluminum salt. When hydrates may be formed depending on the nature of compound, they are also within the scope of this invention.

The therapeutic agent for treatment of herpes virus-derived pain of the present invention can be administered to a mammal in a variety of administration forms. These include, for example, oral preparations, injections, suppositories per rectum, and external preparations (such as ointments, plasters, ophthalmic solutions, etc.). These preparations may be prepared by customary methods per se known by persons skilled in the art. Among oral preparations, solid preparations are prepared, suplatast tosylate is mixed with a vehicle, and optionally, a binder, a disintegrant, a lubricant, a colorant, a sweetener, a flavoring agent, or similar agents, and the resultant mixture is processed into tablets, coated tablets, granules, powders, capsules, dry syrups, etc. by customary methods. When oral liquid preparations are manufactured, suplatast tosylate is mixed with a sweetener, a buffer, a stabilizer, a flavoring agent, or similar agents, and the resultant mixture is processed into, by customary methods, liquid medicines, syrups, etc.

When injections are manufactured, suplatast tosylate is mixed with a pH regulator, a buffer, a stabilizer, an isotonic agent, a local anesthetic drug, or similar agents, and the resultant mixture is processed into injection products for subcutaneous injection, intramuscular injection, or intravenous injection.

Suppositories per rectum are prepared by mixing suplatast tosylate with an excipient, optionally with a surfactant, etc., followed by a routine process for manufacturing suppositories.

Among external preparations, ointments, such as in the form of paste, cream, or gel, are prepared, by mixing a base containing suplatast tosylate with, as required, a stabilizer, a humectant, a preservative, etc., by customary methods. Examples of bases include white Vaseline, paraffin, glycerin, cellulose derivatives, polyethylene glycol, silicone, and bentonite. Examples of preservatives include methyl parahydroxybenzoate, ethyl parahydroxybenzoate, and propyl parahydroxybenzoate.

When plasters are produced, the above-mentioned ointment, cream, gel, paste, etc. are applied onto a customary support by a known method. Supports are preferably woven or nonwoven fabrics made of cotton, staple fiber, or chemically synthetic fiber, and films and foamed sheets prepared from soft vinyl chloride, polyethylene, or polyurethane.

The amount of suplatast tosylate to be incorporated into the above-mentioned dosage forms varies with the patient's symptoms, dosage form etc. It is generally preferred that suplatast tosylate be incorporated into a unit dosage in an amount of about 5 to 1,000 mg for oral agents, about 0.1 to 500 mg for injections, and about 5 to 1,000 mg for suppositories and external agents.

Although the daily dose of suplatast tosylate may also differ depending on the symptoms weight, age, sex or other conditions of a patient, it is preferably about 5 to 1000 mg.

BRIEF DESCRIPTION OF THE DRAWING

FIG. 1 is a graph showing the results of the analgesic test according to the von Frey test along with the time.

BEST MODE OF CARRYING OUT THE INVENTION

The present invention will be described below in more detail with reference to examples and test examples. However, the invention is not limited by these examples.

Preparation Example 1

Tablet suplatast tosylate 50 mg
corn starch 50 mg
microcrystalline cellulose 50 mg
hydroxypropyl cellulose 15 mg
lactose 47 mg
talc 2 mg
magnesium stearate 2 mg
ethyl cellulose 30 mg
unsaturated glyceride 2 mg
titanium dioxide 2 mg Tablets (50 mg of suplatast tosylate/tablet) of the above-described composition were prepared by employing a conventional method.

Preparation Example 2

Granule suplatast tosylate 300 mg
lactose 540 mg
corn starch 100 mg
hydroxypropyl cellulose 50 mg
talc 10 mg Granules (300 mg of suplatast tosylate/package) of the above-described composition were prepared by employing a conventional method.

Preparation Example 3

Capsule suplatast tosylate 100 mg
lactose 30 mg
corn starch 50 mg
microcrystalline cellulose 10 mg
magnesium stearate 3 mg Capsules (100 mg of suplatast tosylate/capsule) of the above-described composition were prepared by employing a conventional method.

Preparation Example 4

Injection suplatast tosylate 100 mg
sodium chloride 3.5 mg
distilled water suitable amount Injections (100 mg of suplatast tosylate/2 ml ampule) of the above-described composition were prepared by employing a conventional method.

Preparation Example 5

Dry Syrup suplatast tosylate 50 mg
purified sucrose 949 mg
fragrance suitable amount A dry syrup (50 mg of suplatast tosylate/package) of the above-described composition was prepared by employing a conventional method.

Preparation Example 6

Syrup suplatast tosylate 50 mg
purified sucrose 1000 mg
ethyl parahydroxybenzoate 1 mg
purified water suitable amount
fragrance suitable amount
colorant suitable amount A syrup (50 mg of suplatast tosylate/2 ml) of the above-described composition was prepared by employing a conventional method.

Preparation Example 7

Suppository suplatast tosylate 300 mg
Witepsol W-35 1400 mg
(Witepsol: registered trademark, product of Dynamite Nobel AG: a mixture of mono-, di-, and tri-glycerides of saturated fatty acids which encompass those acids from lauric acid to stearic acid)

Suppositories (300 mg of suplatast tosylate/piece) of the above-described composition were prepared by employing a conventional method.

Example 1

The Suppression Effect of Suplatast Tosylate Against Diabetic Neuropathy of the Streptozotocin Induced Rat (1) Preparation of the Model for Diabetic Neuropathy By use of male rats with the weight of more than 160 g, 50 mg/kg of streptozotocin (STZ, Sigma-Aldrich Co.) was administered thereto intravenously at the dose of 2 mL/kg to prepare the diabetes model rats induced by STZ (Malcangio M. et al., Pain, 1998). Animals with the blood sugar level of more than 200 mg/dL were adopted as diabetes models. For the measurements of the blood sugar level, the blood (2 µL) collected from the tail vein was measured by use of a measurement chip (Glutest Sensor, Arkray, Inc.) and a portable instrument for measuring blood sugar of Glutest PRO R (Model GT-1661, Arkray, Inc.).

(2) The Von Frey Test

The pain threshold was measured by carrying out the von Frey test on both right and left foot pats of the rats by use of Dynamic Planter Aesthesiometer (Model No. 37400, Ugo Basile, Inc.), and its maximum pressure was set to be 30.0 g, and the arriving time to the maximum pressure was set to be 40 seconds. Eight days after the administration of STZ, the individuals with the pain threshold of higher than a certain level were selected and divided into the groups so that the measured pain thresholds might become even in each group. To the diabetes model rats induced by STZ was administered continuously for one week either 30 mg/kg of suplatast tosylate intraperitoneally or 100 mg/kg of the same orally, and the intraperitoneally administered group and the orally administered group were produced respectively. The diabetes model rats induced by STZ to which solvent (distilled water) was administered orally were designated to the STZ control group. Moreover, the animals of no treatment, i.e. no administration of STZ, to which solvent (distilled water) was administered orally were used as the normal control group. On the 1st, 4th and 7th days after the administration, were measured the pain thresholds of the right and left foot pats for each of the group (8 rats/group), and the analgesic effect was estimated by the threshold of the escape reaction of limb (the total of pain threshold value both of the right and left foot pats). The pain thresholds were measured from 1 to 1.5 hours after the administration, respectively. The Student's test, which is a test for every 2 groups, was applied to the significant difference test of the average value, and the significant level were shown by the following indications:

(Normal control group vs. STZ control group): p value under 0.001%, and

** (STZ control group vs. orally administered group or intraperitoneally administered group): p value under 0.001%

The orally administered group and the intraperitoneally administered group were compared with the STZ control groups, respectively. Moreover, the STZ control groups were compared with the normal control groups, and the establishments of the diabetes neuropathy model were respectively judged.

Results: By the comparison with normal control groups, the nociceptive hypersensitivity appeared significantly at the STZ control groups and the symptom continued from the first day of the measurement to the 7th day (p value under 0.001%). The establishment of the diabetes neuropathy model induced by STZ was confirmed by these facts. The analgesic effects were not found on the first day of the measurement (at the first dose) in both of the animal models to which 30 mg/kg (intraperitoneal administration) and 100 mg/kg (oral administration) of suplatast tosylate were respectively administered. On the other hand, significant suppression effects of neuropathy (p value under 0.001%) were found on the 4th day (4 days after the administration of suplatast tosylate) and the 7th day (7 days after the administration) at both of 30 mg/kg (intraperitoneal administration) and 100 mg/kg (oral administration) groups.

From the results mentioned above, it has become clear that suplatast tosylate shows an excellent analgesic effect against a throbbing pain accompanied with the diabetic neuropathy.

INDUSTRIAL APPLICABILITY

The therapeutic agent of this invention shows an excellent effect against the diabetic neuropathy, especially against a throbbing pain accompanied with the diabetic neuropathy, with almost free from the harmful side effect, and therefore is very useful.

The invention claimed is:

1. A method of treating diabetic neuropathy comprising administering to a mammal an effective amount of (±)-[2-[4-(3-ethoxy-2-hydroxypropoxy)phenylcarbamoyl]-ethyl]dimethylsulfonium p-toluenesulfonate of formula (1)

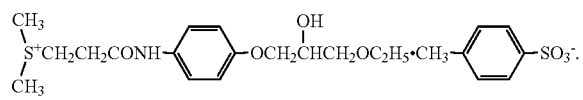

(1)

* * * * *